(12) United States Patent
Cobb

(10) Patent No.: US 6,786,906 B1
(45) Date of Patent: Sep. 7, 2004

(54) ELECTROSURGICAL CUTTING TOOL

(75) Inventor: Garry Vincent Cobb, Long Eaton (GB)

(73) Assignee: Nuvotek Ltd., Leeds (GB)

( * ) Notice: Subject to any disclaimer, the term of this patent is extended or adjusted under 35 U.S.C. 154(b) by 0 days.

(21) Appl. No.: 09/719,970

(22) PCT Filed: Jun. 17, 1999

(86) PCT No.: PCT/GB99/01809
§ 371 (c)(1),
(2), (4) Date: Dec. 18, 2000

(87) PCT Pub. No.: WO99/65378
PCT Pub. Date: Dec. 23, 1999

(30) Foreign Application Priority Data

Jun. 17, 1998 (GB) ................................................ 9813042

(51) Int. Cl.7 ............................ A61B 18/18; A61F 7/12
(52) U.S. Cl. ........................................... 606/37; 607/98
(58) Field of Search ............................. 606/37, 34, 48, 606/38, 45, 1; 607/1, 96, 98, 99, 115

(56) References Cited

U.S. PATENT DOCUMENTS

| 5,669,907 | A  |   | 9/1997  | Platt, Jr. et al. |        |
|-----------|----|---|---------|-------------------|--------|
| 5,817,091 | A  | * | 10/1998 | Nardella et al.   | 606/38 |
| 6,004,319 | A  | * | 12/1999 | Goble et al.      | 606/48 |
| 6,228,081 | B1 | * | 5/2001  | Goble             | 606/34 |
| 6,287,304 | B1 | * | 9/2001  | Eggers et al.     | 606/37 |
| 6,383,183 | B1 | * | 5/2002  | Sekino et al.     | 606/34 |
| 6,402,747 | B1 | * | 6/2002  | Lindemann et al.  | 606/42 |
| 6,416,509 | B1 | * | 7/2002  | Goble et al.      | 606/37 |

FOREIGN PATENT DOCUMENTS

| EP | 0 521 501 A2  | 7/1992 |
|----|---------------|--------|
| WO | WO 90/07303   | 7/1990 |
| WO | WO 97/03619   | 2/1997 |

* cited by examiner

Primary Examiner—Thomas Denion
Assistant Examiner—Daniel Robinson
(74) Attorney, Agent, or Firm—Woodard, Emhardt, Moriarty, McNett & Henry LLP

(57) ABSTRACT

The invention relates to an electrosurgical tool which includes in a housing an active and return electrode which can be controlled in use so that it is the active electrode which performs the electrosurgical function in contact with the body tissue. The tool may be controlled with the return electrode in contact with the body tissue but preferably not in contact with the body tissue. The return electrode is typically formed from a number of components spaced with respect to the active electrode.

13 Claims, 16 Drawing Sheets

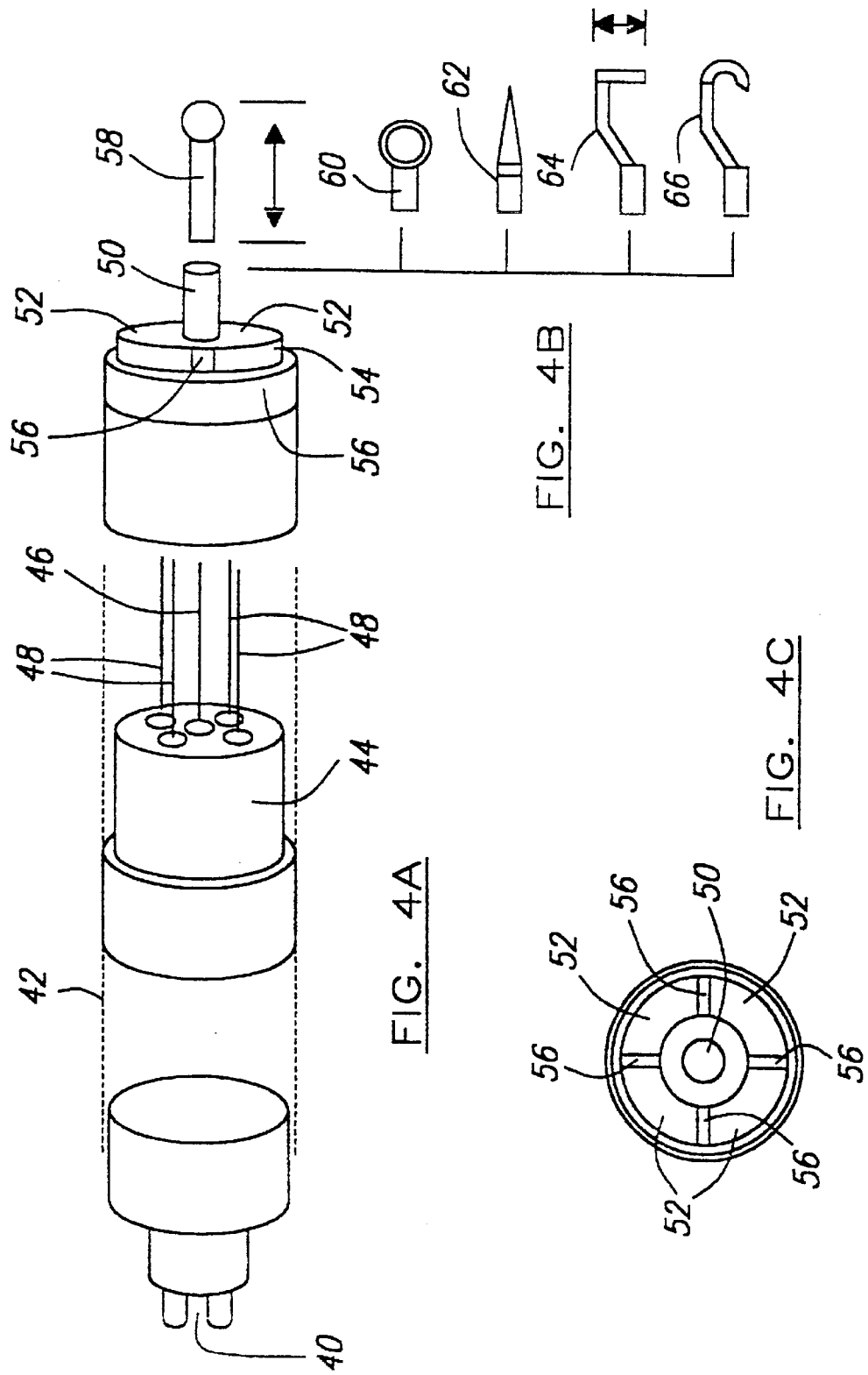

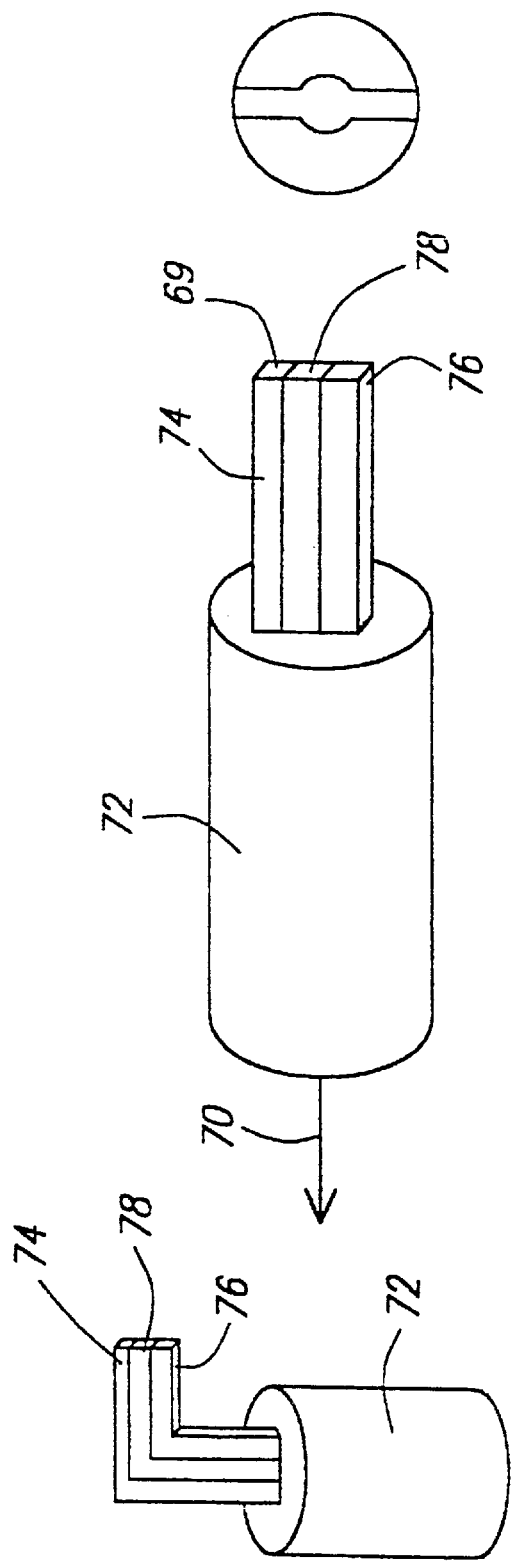

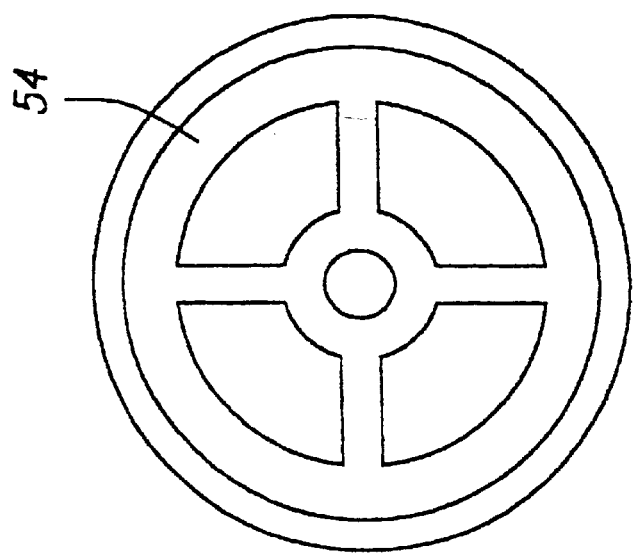
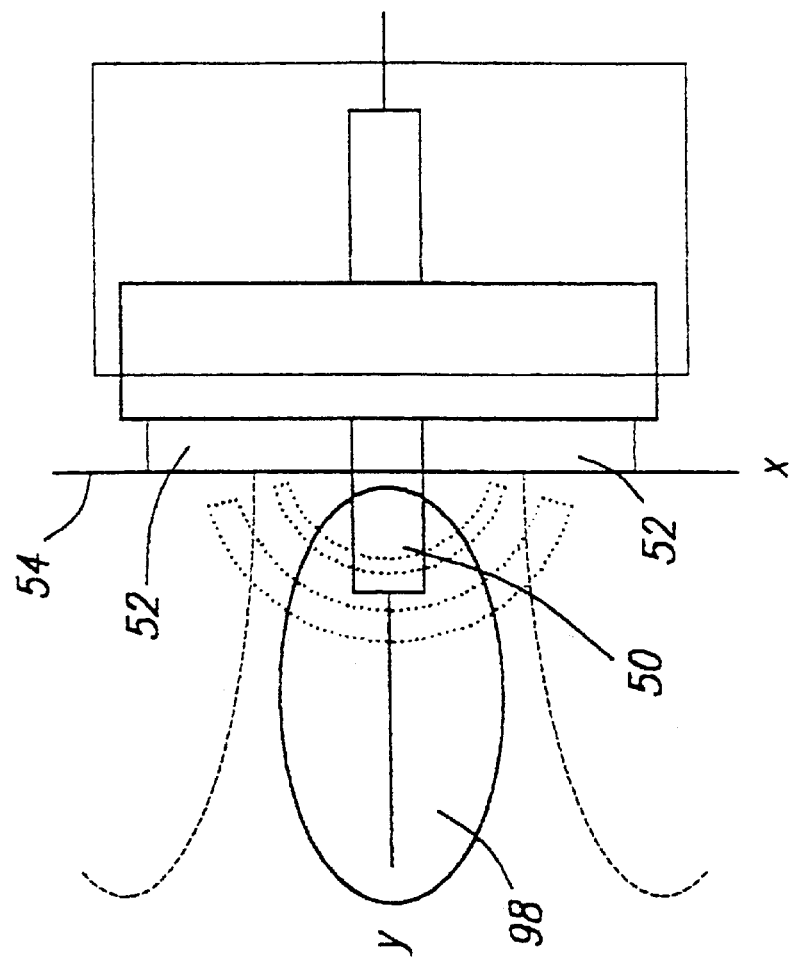
FIG. 8A
FIG. 8B

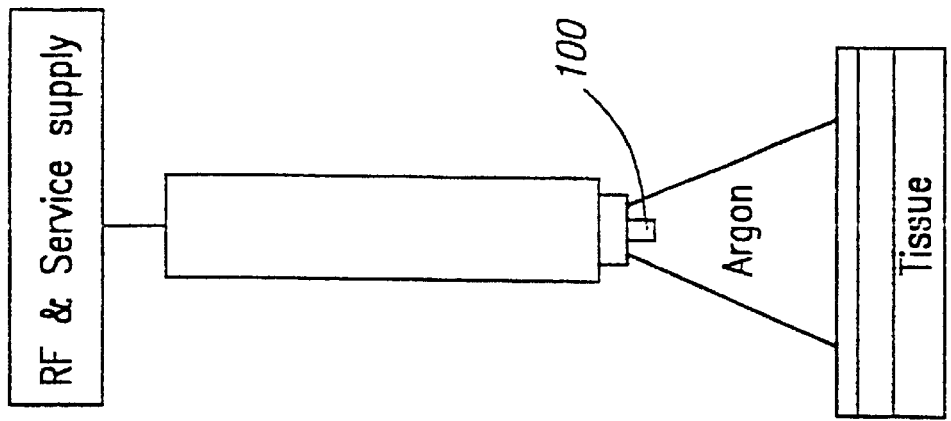
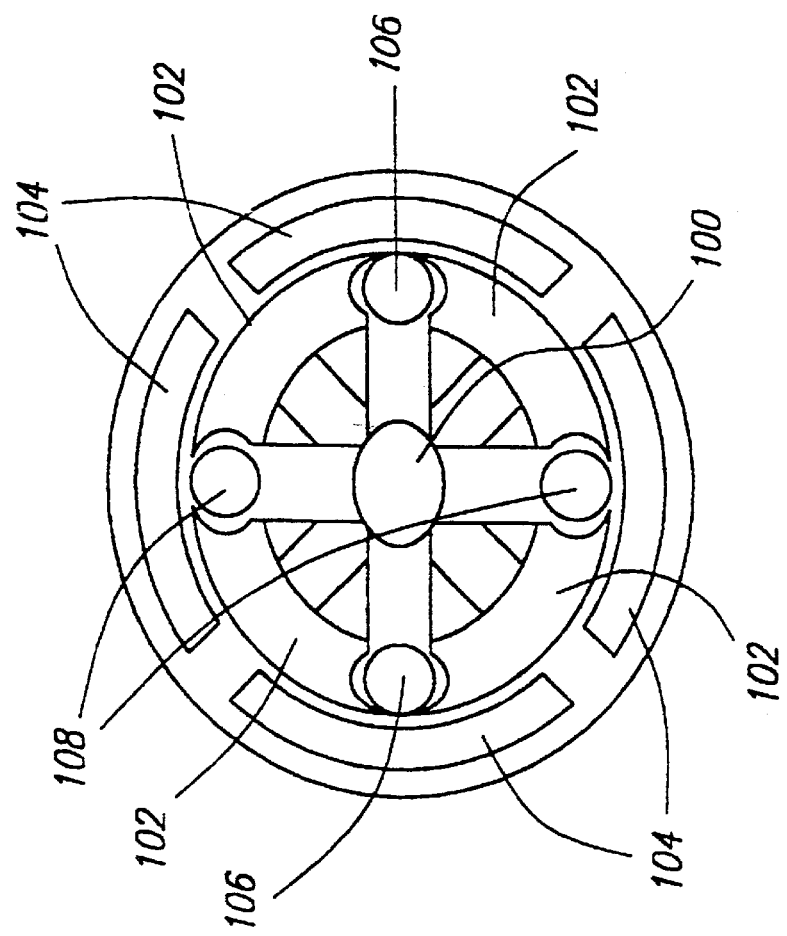
FIG. 13B

ELECTROSURGICAL CUTTING TOOL

The invention which is the subject of the application is an electrosurgical tool of a type which can be used to perform electrosurgical functions such as incisions and/or coagulation of body tissue and/or fluids and can be used in conjunction with electrical generating and control apparatus to provide an advantageous function such as cutting and/or coagulating operation to be performed.

Electrosurgery is generally defined as the use of radio frequency (RF) current to cut tissue and control bleeding and the process has been employed in open operative procedures for many years and it has become the most widely used cutting and coagulation technique for minimally invasive surgery.

In conventional electrosurgical cutting apparatus, and in particular cutting tools, it is known to utilise a cutting tool having an active or supply electrode and a second, or return, electrode. In one arrangement the return electrode is provided in the form of a plate upon which the patient on whom the surgery is being performed lies. This can be dangerous to the patient and can, upon malfunction, cause burns.

Though versatile, cost effective, and popular, electrosurgery techniques can compromise patient safety under certain circumstances. The surgeon may directly burn non-targeted internal organs or tissue upon unintended contact of the tip of the tool through imprecise mechanical operation of a laparoscopic instrument. In addition stray electrical currents emanating from the tool can inadvertently burn non-targeted tissues beyond the surgeon's limited field of vision and such stray energy burns can occur regardless of the surgeon's skill and judgement. Stray electrical currents may be released either through direct coupling or if the electrical insulation that coats the active electrode fails due to degradation or damage. Another electrical phenomenon known as capacitive coupling can instantaneously transfer significant amounts of stray electrical current to non-targeted tissue, causing injuries which are located outside the restricted keyhole view of the laparoscope, and thus may go undetected by the surgeon. The symptoms of injury can be delayed in onset for several days, thereby obscuring the underlying cause. The complications resulting from internal electrosurgical burn injuries compounded by delay in diagnosis and treatment can have a profound medical and economic impact on patients. Electrosurgical burns can also result from the phenomenon of capacitive coupling, which occurs when electrical current is induced from the active electrode to nearby conductive material, despite intact insulation. During electrosurgery, the charge on the active electrode switches from highly positive to highly negative at a very high frequency. The rapidly varying electrical field around the active electrode is only partially impeded by electrical insulation and creates stray electrical currents by alternately attracting and repelling ions in surrounding body tissue. Currents transferred in this way in nearby tissue can cause irreversible damage. The movement of electrically charged ions in capacitively coupled tissue can cause currents that can heat tissue sufficiently to produce a burn. Thus it is clear that the combination of the design of the conventional instruments, the limited field of vision during laparoscopy, and the nature of the electrosurgical environment, can cause even the most skilled surgeon to inadvertently burn a patient.

One commonly used type of electrosurgery is known as Monopolar electrosurgery, and a diagram illustrating this is included as Prior Art Diagram 1, which has traditionally been used primarily as a method of hemostasis during surgery. The technique gets its name from the single electrode used to delivery electrical energy from the current generator to the patient. A concentrated electrical current is delivered from the tip of the electrode to targeted tissues, causing a controlled burn that stops bleeding. With this technique, the electricity then disperses and flows through the patient, to be returned to the electrosurgical unit (ESU) via a large return electrode pad or plate attached to the patient's skin at a remote location. By varying the voltage, current, or waveform of the electrical energy delivered by the electrode, surgeons can cut tissue cleanly (a "pure cut"), coagulate tissue to stop bleeding, or produce a "blended cut" that combines these two functions. Finally, a dispersed coagulation mode known as fulguration allows coagulation of diffuse bleeding, which may be desirable when operating on highly vascular tissues. This range of surgical modes, in addition to superior efficacy for coagulation, makes Monopolar electrosurgery the dominant and most advantageous minimally invasive surgery technique.

An alternative form of electrosurgery is bipolar electrosurgery, and a diagram of the same is included as prior art diagram 2, in which there is provided a tool on which both the active and return electrodes are mounted, delivering energy to tissues between the two electrodes upon contact with the tissue by the two electrodes so that the electrosurgical function takes place between the two electrodes and which causes the frequent blockage between the two electrodes due to cut body tissue and other material and therefore means that there is frequent inability to perform the electrosurgical function as both electrodes are required to actually perform the function. Unlike Monopolar electrosurgery, bipolar electrosurgery is not an effective method for making a "pure cut." Furthermore, the bipolar technique cannot be used to stop bleeding over a large area. In order to achieve hemostasis in bipolar surgery, it is necessary to grasp tissue between both the active and return electrodes.

The aim of the present invention is to provide an improved electrosurgical tool which can be used for electrosurgical work with the electrodes mounted within the tool in a manner which allows improved operation and control of the same. It is also particularly sought that the tool can be operated with a control means which analyses and reacts to impedance characteristics of the tissue during operation of the apparatus and controls the power supply to the tool in response to analysis and interpretation of the same.

In a first aspect of the invention there is provided an electrosurgical tool, said tool comprising a housing in which is provided electrical connections to a power supply, and the tool includes a supply or active electrode, and a return electrode, and a working end for performing an electrosurgical function, and wherein the working end is formed by the end of the active electrode and return electrode and the active electrode performs the electrosurgical function.

In one embodiment the active electrode in use is in contact with the body tissue of a patient and there is a gap between the end of the return electrode of the tool and the body tissue. Typically the working end of the active electrode protrudes beyond the working end of the return electrode. In one preferred embodiment the supply or active electrode is mounted in the tool so that the end of this electrode protrudes beyond the end of the housing.

Typically in whichever embodiment of the tool, in the supply of power to the tool from the generator to which it is connected there is a change in phase between the active and return electrodes in use of the electrosurgical tool.

In a further embodiment, the ends of both the active and return electrodes contact the body tissue and in this embodiment the return electrode is positioned on the body tissue prior to the active electrode so as to minimise risk of burn to the patient.

Typically, the active electrode is mounted within and substantially surrounded by the return electrode which in one preferred arrangement is formed in a substantially annular form with the active electrode mounted to pass through the centre of the same. In one arrangement the return electrode comprises a series of components in one example, four electrode components, each provided to lie within 90 degree sectors of the annular arrangement. Typically the ends of the components of the return electrode are angled and/or curved to control the directivity of the RF field generated at the working end of the tool.

Typically the return electrode components are arranged in pairs of phased positive and negative arrangements. In one embodiment two of the four components are provided as phased negative components and two are phased positive components.

Typically the active electrode is spaced from contact with the return electrode arrangement. In one embodiment the spacing is maintained by insulating material which can be of any material which can withstand the voltage being applied along the electrodes. In one embodiment the material used is a ceramics material.

It is envisaged that the electrodes are mountable in a body which is formed of an insulating material, in one embodiment by moulding, and which body is provided with means to allow the same to be electrically connected to the electrodes. It is envisaged that the electrodes can be manufactured of any suitable material, one being high grade stainless steel. Typically the housing of the tool is releasably attached with the body thereby allowing the housing to be connected to a body of the required length for the surgical work to be performed and so the housing may be connected to a number of different tool bodies. The housing is typically formed from tubing such as stainless steel tubing and this surrounds the insulating material and the electrodes.

The housing or body can also, in one embodiment, be provided with engagement and electrical contact means into which the return and/or active electrode can be inserted. The housing is also provided with electrical contact and mechanical engagement means which allow the housing to be connected mechanically and electrically to the tool body.

In one embodiment the active electrode is provided with a surgical formation at the working end which, when the electrode is in position, protrudes from the tool and is formed to allow a specific electrosurgical function to be performed. Typically a range of electrodes with differing surgical formations can be provided and fitted to suit specific requirements and said surgical formation can include knife edge, point, ball or hook formations. The surgeon can therefore interchange electrodes to suit particular surgical requirements. In an alternative embodiment a common electrode can be used with engagement means to allow engagement with any of a range of surgical formations at the working end.

The tool in accordance with this invention can be used in various embodiments for use in open surgery, minimal access surgery, Neurosurgical and transluminal percutaneous treatment of vessel occlusion and speciality surgical fields In a further aspect of the invention there is provided an electrosurgical tool, said tool comprising an active electrode and a return electrode in parallel and connected to an electric current and electric current control means and characterised in that the electrical current is split using a biphasic RF output and the split is controlled in response to the impedance measurement of the active electrode.

In one embodiment the biphasic array of the return electrode within the RF/EM field is used as the return pathway and the Radiofrequency [RF] energy is directed using impedance controlled by a biphasic RF/EM Field surrounding a central or offset active electrode.

In one embodiment the electrosurgical tool in accordance with this invention is used in conjunction with a control means in the form of an electrosurgical generator which utilises dynamic impedance feedback and adaptive algorithm techniques together with a waveguided biphasic RF/EM energy to generate a phased energy field around the active electrode of the tool. One such electrosurgical generator is described in the applicants patent EP0830095.

Specific embodiments of the invention will now be described with reference to the accompanying drawings wherein:

Diagram 1 is a view of monopolar electrosurgery delivering electro energy from a current generator to the patient.

Diagram 2 is a view of bipolar electrosurgery wherein the active and return electrodes are mounted on a tool and contact the patient.

Figure 9:
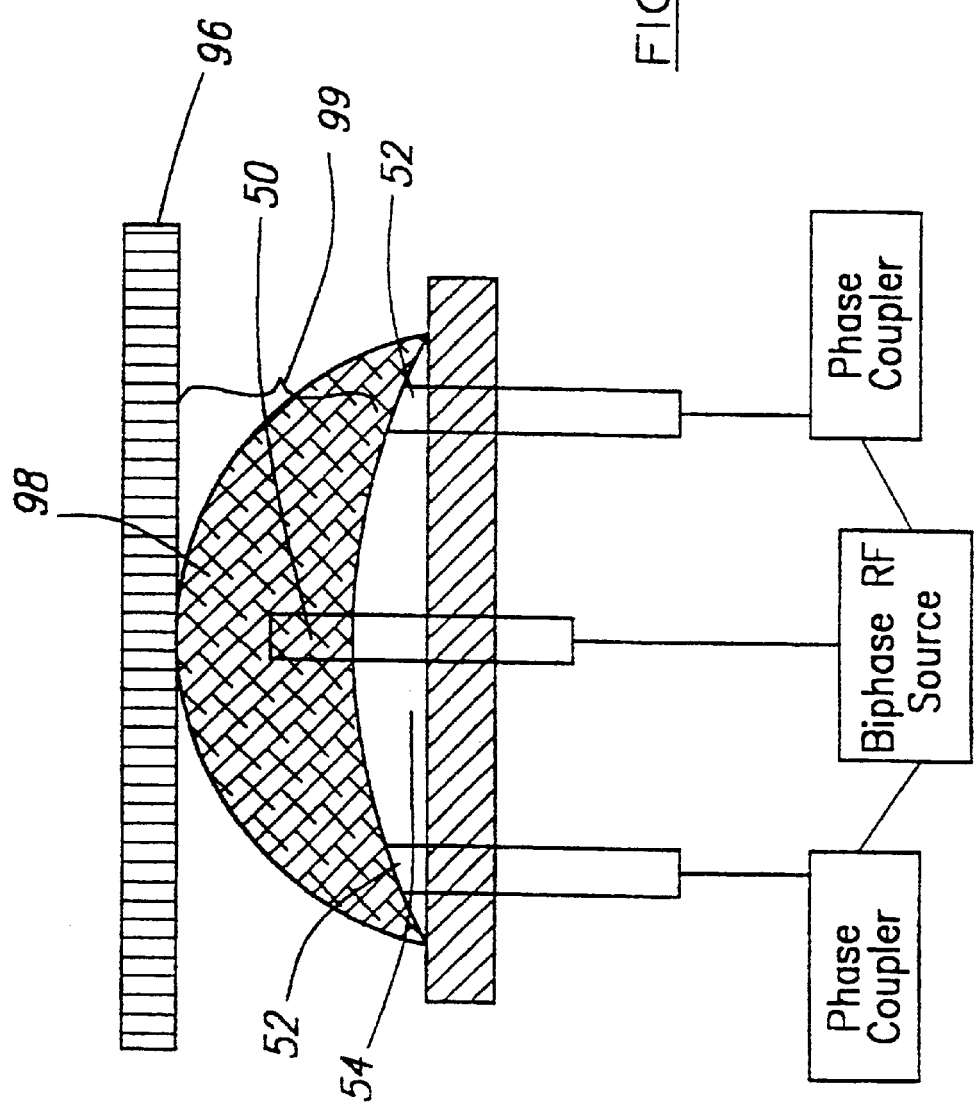
Figure 10:
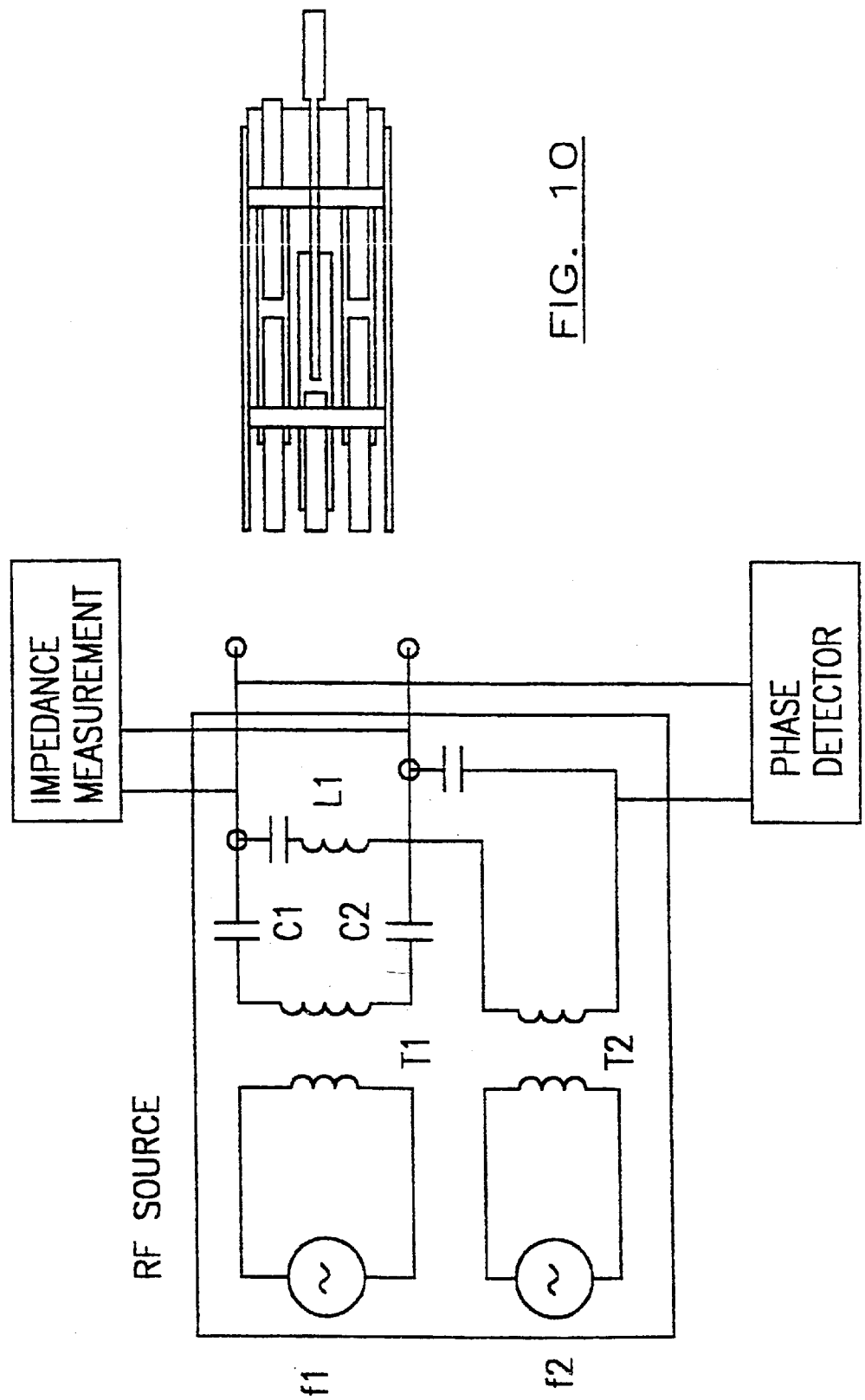
Figure 11A:
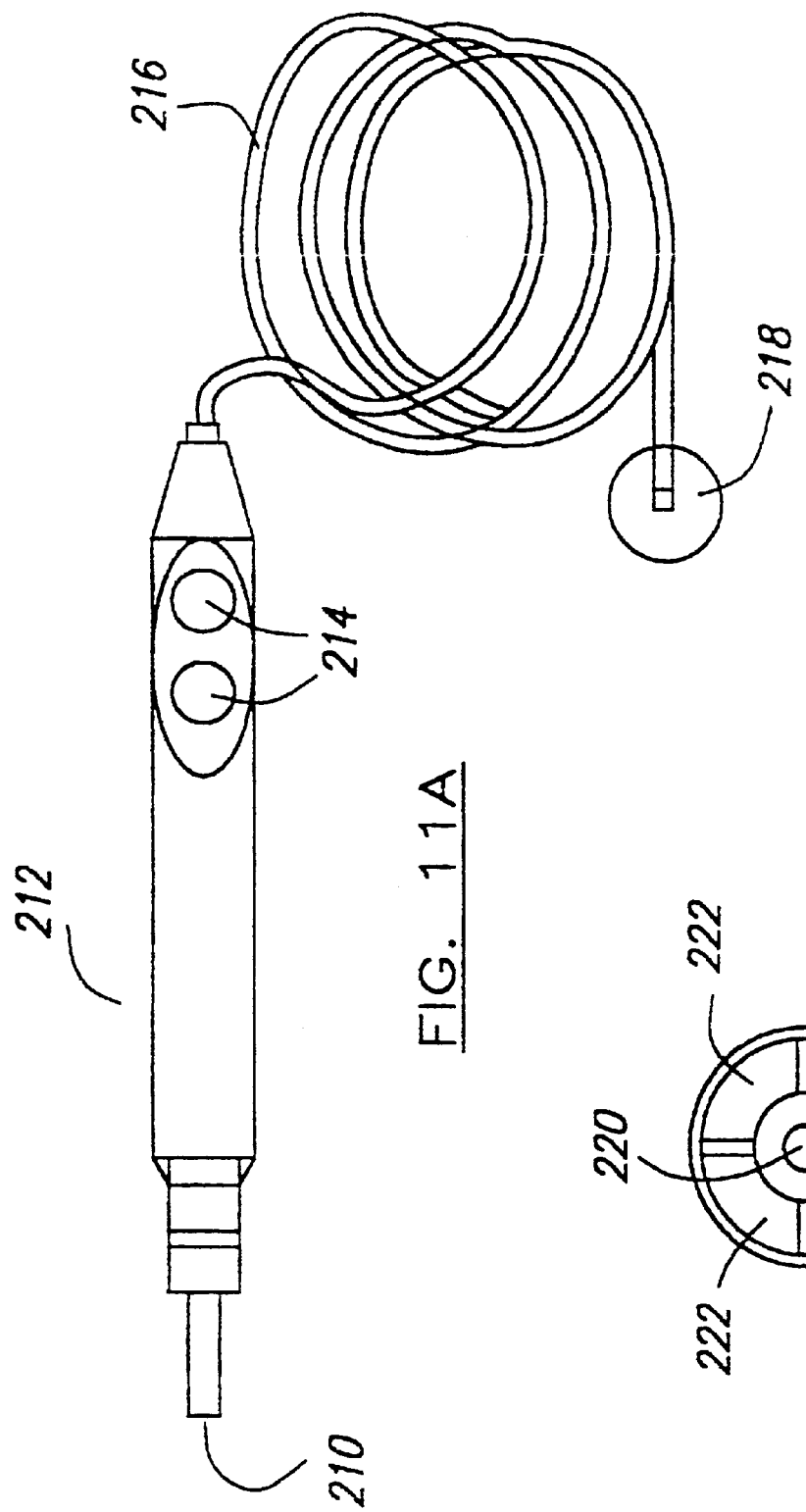
Figure 11B:
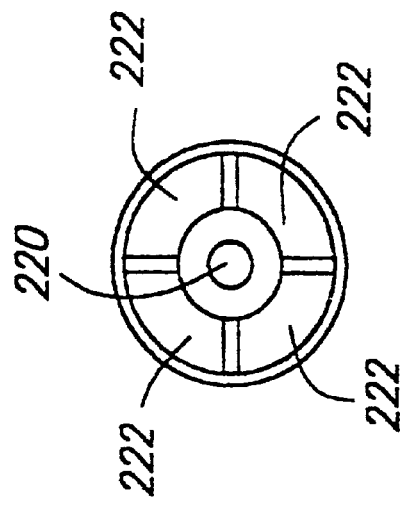
Figure 12A:
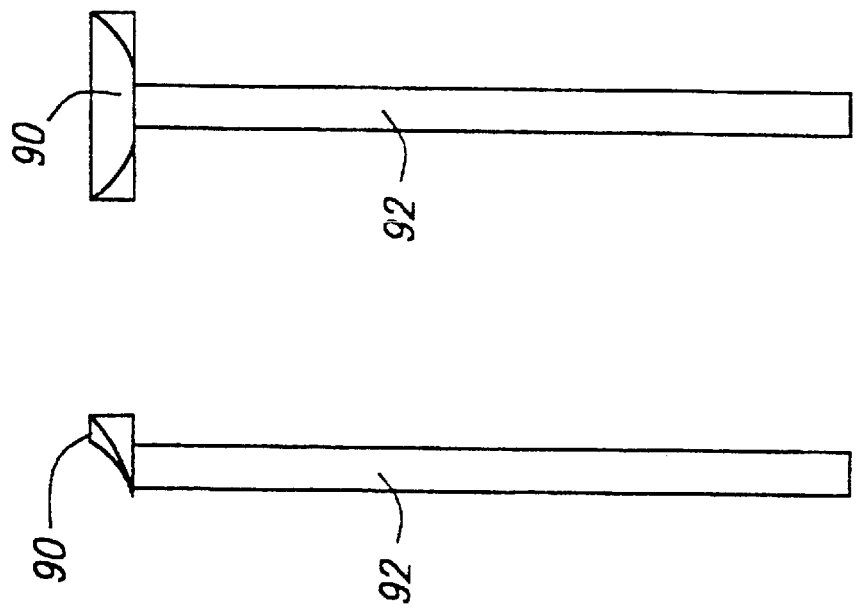
Figure 12B:
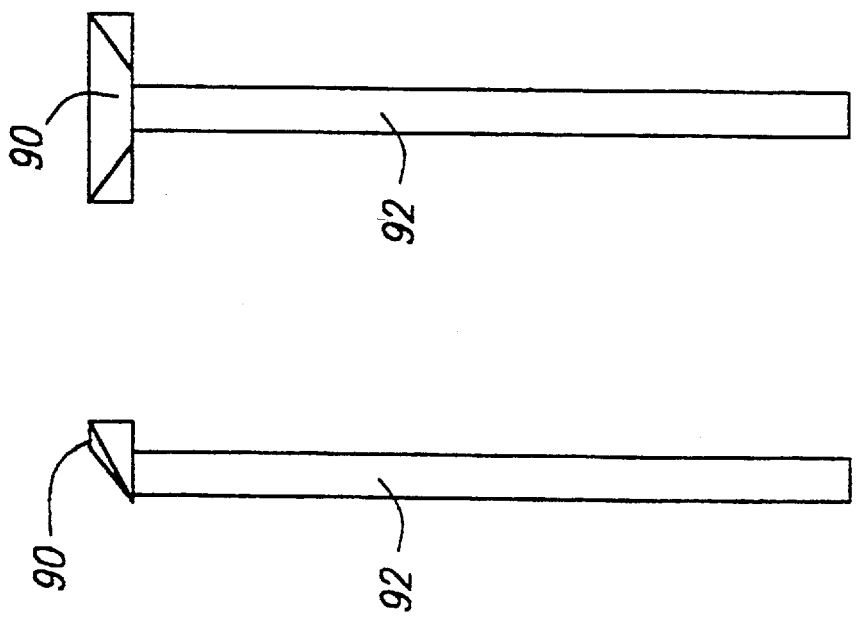
Figure 13A:
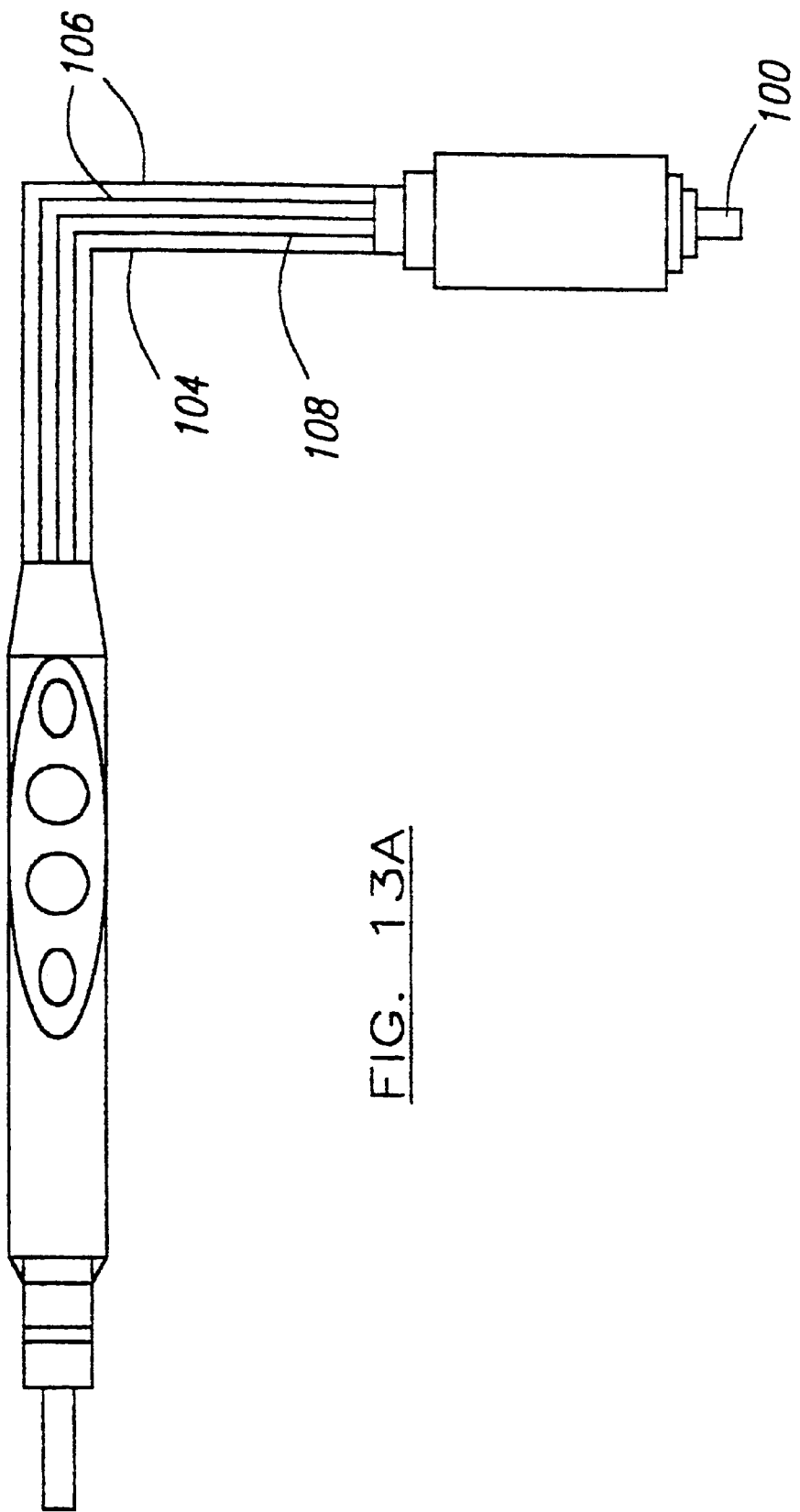

FIGS. 4A–C illustrate a further embodiment of an electrosurgical tool according to the invention;

FIGS. 5a–d illustrate alternative embodiments of the electrode arrangement for the tool;

FIGS. 6A–C illustrate a yet further embodiment of the tool for use in a bipolar style format;

FIGS. 7a–f illustrate yet further embodiments of electrode arrangement;

FIGS. 8 and 9 illustrate arrangements of electromagnetic field generated between the tool in accordance with the invention and body tissue when in use;

FIG. 10 illustrates one operating system for a tool in accordance with the invention;

FIGS. 11a–b illustrate an alternative embodiment of the tool of the invention;

FIGS. 12a–b illustrate the shape and form of a return electrode component in one embodiment; and FIGS. 13a–b illustrate one form of the tool in a form for use.

Figure 15:
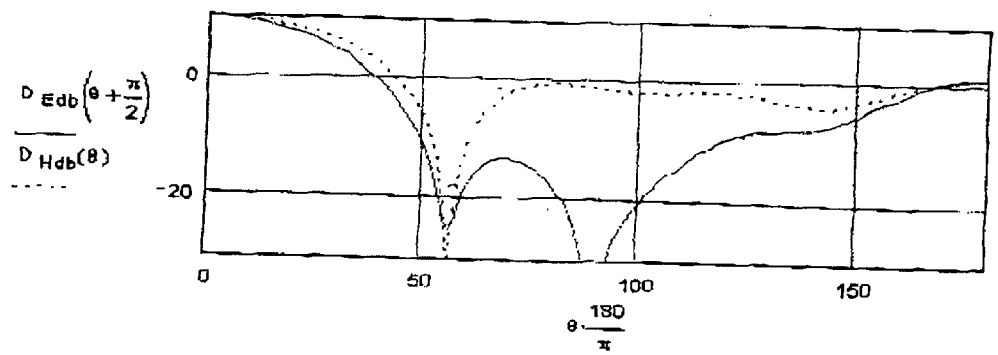

FIG. 15 is a x-y graph of multipolar array directivity.

Figure 16:
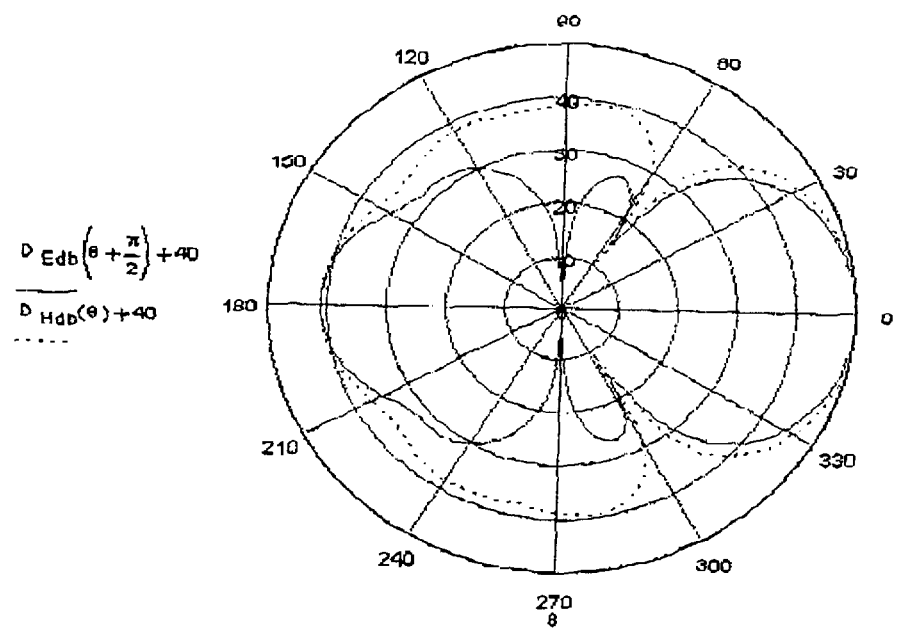

FIG. 16 is a polar graph of multipolar array directivity.

Figure 17:
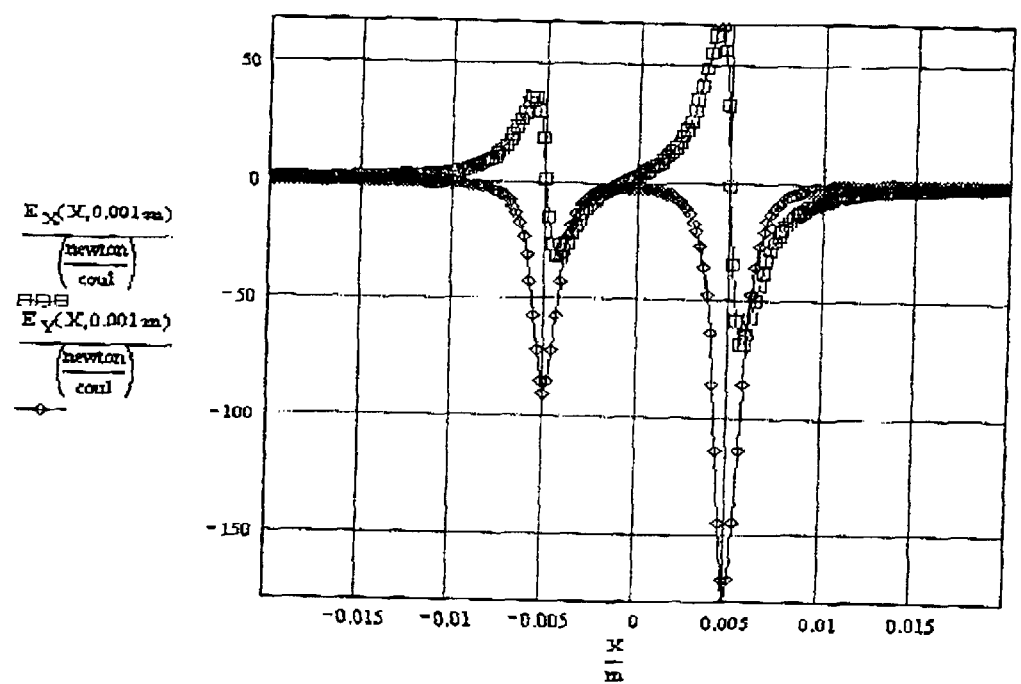

FIG. 17 is a graph of the net electric field as a function of X and Y=0.00

Figure 18:
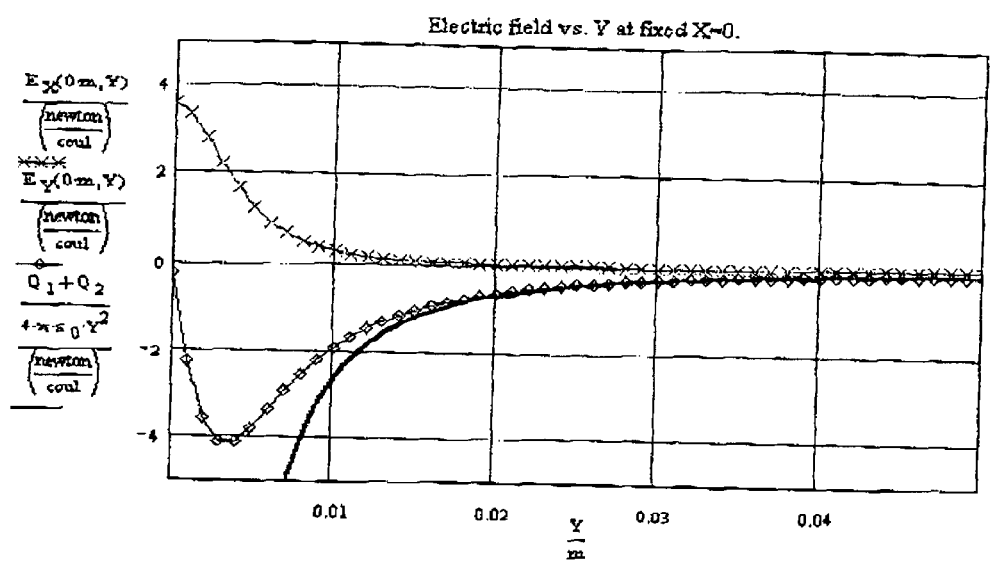

FIG. 18 is a graph that shows the electric field variation along a line perpendicular to the X axis and showing that for Y>>L the electric field variation is as if there was a single point charge.

Figure 19:
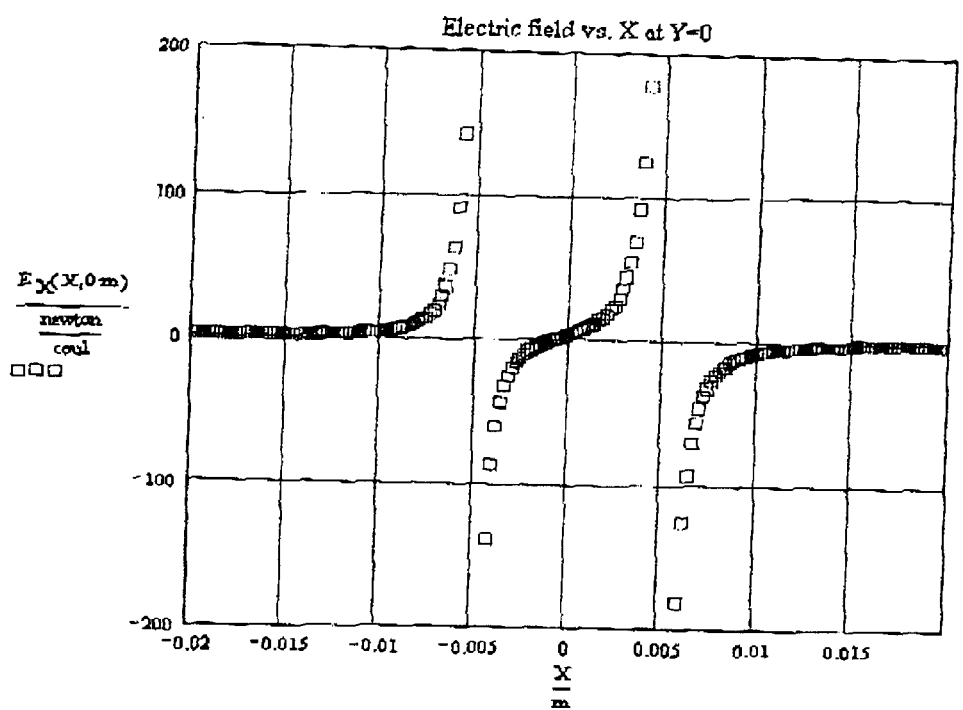

FIG. 19 is a graph that shows the electric field variation with X for Y=0.

Figure 1:
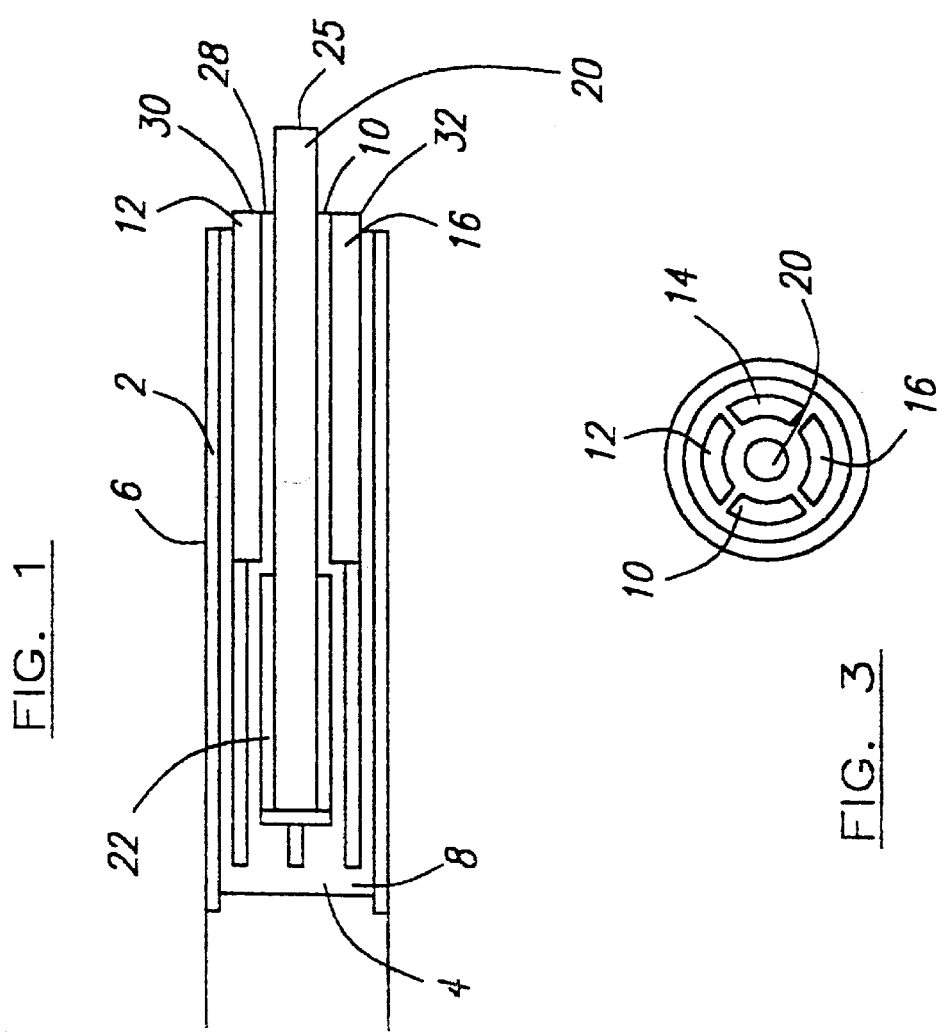
FIG. 1 illustrates a sectional elevation of a housing of an electrosurgical tool according to the invention.

Referring firstly to FIG. 1 there is illustrated a sectional elevation of a housing 2 for attachment to a body 4 (partially shown) to form an electrosurgical tool according to one embodiment of the invention. The body 4 is provided with electrical connections (not shown) which provide the power from an electrical power generator and control means and allow measurements for the control of the tool to be returned to the control means. This function is not described in detail but can preferably be of a form described in the applicants co-pending patent no. EP0830095. There are also provided contact means which may be in the form of an adapter (not shown) which allow the mechanical and electrical connection of the housing 2 with the body 4 to form an electrosurgical cutting tool according to the invention.

Figure 2:
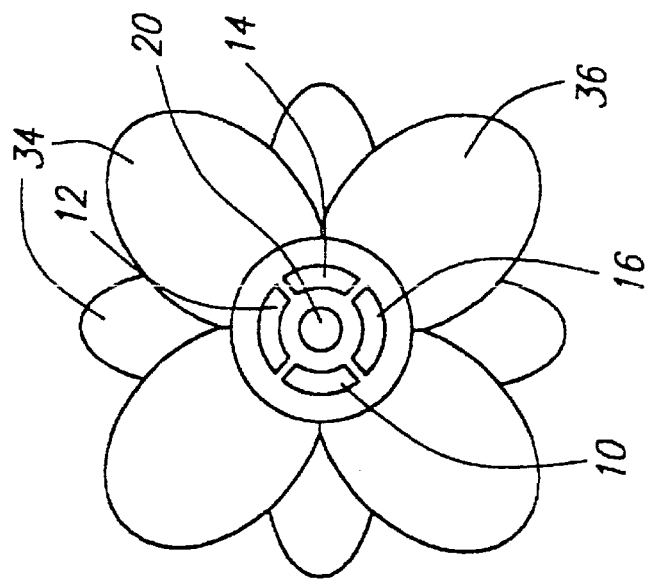
FIG. 2 illustrates a diagrammatic end view from the end of the housing.
Figure 3:
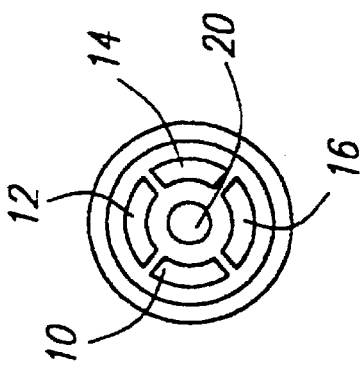
FIG. 3 illustrates a sectional end view of the housing.
Figure 5A:
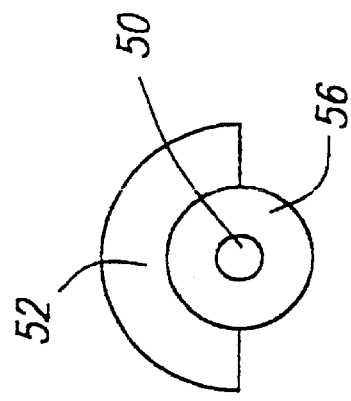
Figure 5B:
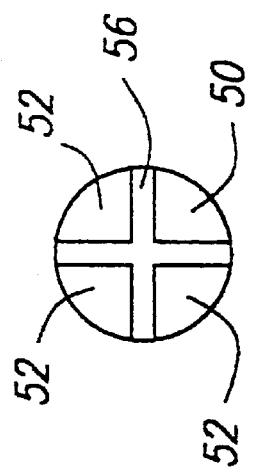
Figure 5C:
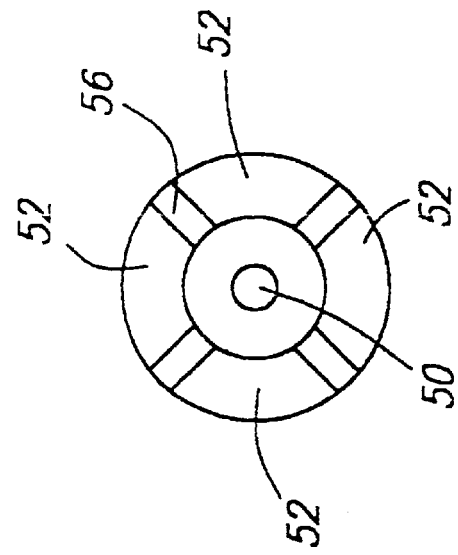
Figure 5D:
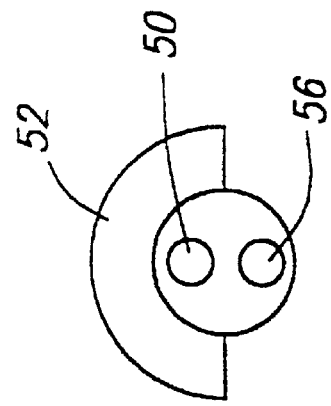
Figure 7A:
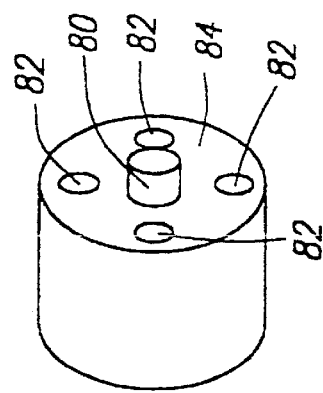
Figure 7B:
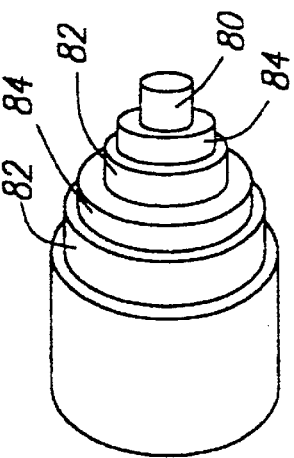
Figure 7C:
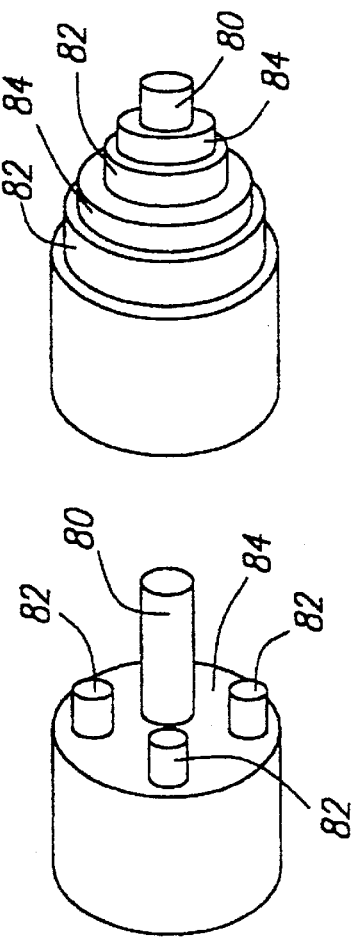
Figure 7D:
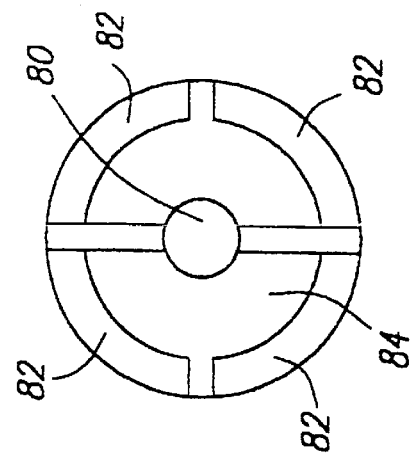
Figure 7E:
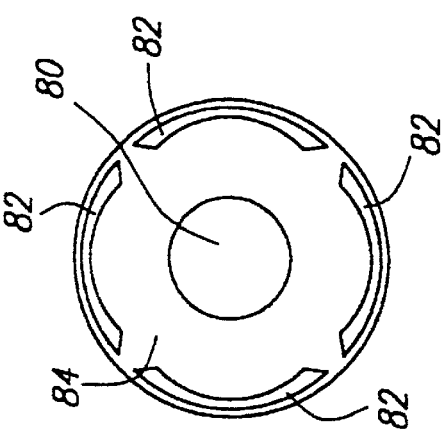
Figure 7F:
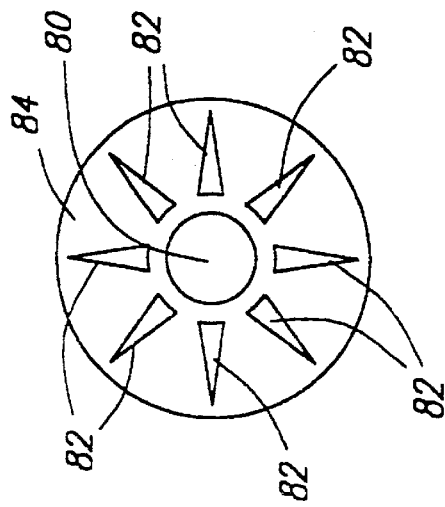

The housing 2 is formed by an outer tube 6 which can be of stainless steel, and the tube surrounds at least a portion of the body 4 which is formed of an insulating material 8 which can in one embodiment be a moulded ceramic material. Within the insulating material is a return electrode arrangement which, in the embodiment shown in FIGS. 1–3 comprises components 10–16. The FIGS. 2 and 3 show how the components, in end elevation, are each curved about approximately 70–90 degrees to form a substantially annular arrangement, with each of the components edges separated by the insulating material 8. In the embodiment shown the electrodes 10 and 12 are phased negative electrodes and the electrodes 14 and 16 are phased positive electrodes.

Mounted within the centre of the annular return electrode arrangement is the supply or active electrode 20 and which can be inserted into the body 4 insulating material 8 to contact with an electrical contact 22. It will be seen in FIG. 1 that the working end 24 of the active electrode protrudes beyond the ends 28,30,32 of the electrode portions 10,12,16 respectively and, although not shown, electrode portion 14. It is the end 25 of the electrode 20 at the working end 24 of the tool which is used to perform the electrosurgical function. As will be explained with reference to the following drawings, the end 24 of the electrode 20 can have a required surgical formation such as a knife, point, ball or hook as required to perform the particular surgical work and so it will be appreciated that the electrode 20 or at least the end of the same can be changed for another electrode with a different surgical formation as appropriate.

FIG. 2 illustrates how, in operation, the arrangement between the active electrode and return electrode arrangement allows the creation of phased dipolar fields y and x, 34,36 respectively, as illustrated and this allows only the tip of the active electrode to contact the body tissue rather than both electrodes as conventionally required and thus provides a considerable advantage over conventional cutting tools.

FIGS. 4A–4C illustrate a more detailed view of an electrosurgical tool in accordance with the invention wherein the tool comprises an RF source connection 40 to allow the tool to be connected to a generator power supply, a housing or skin 42 in which the components of the tool are housed and which comprise a body having a capacitive shield 44 which in one embodiment is of PTFE material, and a series of electrical connections 46, 48. The connection 46 is provided to connect with the active electrode 50 of the tool and the connections 48 connect with the return electrode components 52 at the front or working end 54 of the tool. It is shown how the return electrode components are separated, and separated from the active electrode, by insulating material in the form of a ceramic substrate 56 and how the active electrode is positioned so as to be surrounded by the return electrode components 52. It is also shown how the active electrode protrudes from the end 54 of the tool. In one embodiment a number of active electrodes can be available for selected use, each having a surgical formation at the working end, and various options are shown and referenced 58–66. Alternatively a common electrode can be provided with engagement means to allow the working end to have one of the surgical formations referenced 58–66 attached thereto. These surgical formations shown are known as Ball electrode, Wire loop electrode, needle electrode, MIS hook electrode and MIS J hook electrodes respectively which are selectively used to perform a range of electrosurgery functions. These surgical formations are illustrated as examples only and it should be appreciated that any electrosurgical working end formation can be used with the tool in accordance with the invention since the density of charge on the surface of the active electrode is inversely proportional to the radius of curvature at the electrode surface.

FIGS. 5A–D illustrate end views of alternative embodiments of the tool working end 54 and illustrate the manner in which the active electrode 50 and return electrode components 52 can be provided in different geometrical arrangements to suit particular requirements and operating conditions and how the ceramic substrate 56 which separates the return electrode components and the active electrode can be shaped to suit requirements.

FIGS. 6A–C illustrate a further embodiment of a tool for operation with a biphasic generator and wherein in this case the tool has an RF connection 70 to a generator, a variable length body 72 and in which there is provided a first or active electrode 74 and a second or return electrode 76 which is separated from the first by a substrate of ceramics material 78. In this case the active and return electrodes are both provided at the working end 69 in the same plane so that in use the working ends of both the active and return electrodes contact the tissue. However by the use of the generator to control the phase change between the two electrodes only the active electrode 74 actually performs the electrosurgical function on the body tissue and therefore overcomes the problem of foreign matter blockage between electrodes as with the conventional bipolar form of tools as capacitive coupling between the active and return electrodes is prevented.

FIGS. 7A–F illustrate yet further arrangements of the working end of the tool in accordance with the invention where there is shown in each instance the active electrode 80, return electrode components 82 and ceramic separating means 84.

The electrodes of the tool can be arranged in a number of embodiments to provide a tool for particular requirements and the tool itself can be flexible or rigid but in each case the similar operating characteristics and control is adopted.

The shape of the working ends 90 of the return electrode components can be both angled and curved as is illustrated in FIGS. 12a–b which show two embodiments of return electrode components 22. This angled curvature is provided to correspond with a calculated degree of hyperbole which in turn determines the E and H plane directivity of the RF ion field which are two planes of the ion field. A method of calculating the required form of the return electrode components in terms of angle of hyperbole is described below.

One method of calculating multipolar electrode dipolar array directivity

This equation computes the net electric field components Ex and Ey created by two Dipolar charges Q1 and Q2. The charges are located on the x axis at x=−L/2 and at x=L/2, respectively. The field components versus x for fixed y and versus y for fixed x are graphically shown.

The electric charges expressed in coulombs.

$$\text{Permitivity constant: } \varepsilon_0 := 8.85 \cdot 10^{-12} \cdot \frac{\text{coul}^2}{\text{m}^2 \cdot \text{newton}}$$

$Q_1 := -10^{-14} \cdot \text{coul}$ $Q_2 := -2 \cdot 10^{-14} \cdot \text{coul}$ Distance between charges in meters: $L := 0.01 \cdot m$ $X := -0.02 \cdot m,$ $\quad\quad\quad\quad Y := .0001 \cdot m, .0011 \cdot m \ldots 0.2 \cdot m$ $-0.0198 \cdot m \ldots 0.02 \cdot m$ The electric field created by the two charges at the point (X,Y) expressed in N/C.

$$E_X(X, Y) := \frac{Q_1}{4 \cdot \pi \cdot \varepsilon_0} \cdot \frac{X + \frac{L}{2}}{\left[\left(X + \frac{L}{2}\right)^2 + Y^2\right]^{\frac{3}{2}}} + \frac{Q_2}{4 \cdot \pi \cdot \varepsilon_0} \cdot \frac{X - \frac{L}{2}}{\left[\left(X - \frac{L}{2}\right)^2 + Y^2\right]^{\frac{3}{2}}}$$

$$E_Y(X, Y) := \frac{Q_1}{4 \cdot \pi \cdot \varepsilon_0} \cdot \frac{Y}{\left[\left(X + \frac{L}{2}\right)^2 + Y^2\right]^{\frac{3}{2}}} + \frac{Q_2}{4 \cdot \pi \cdot \varepsilon_0} \cdot \frac{Y}{\left[\left(X - \frac{L}{2}\right)^2 + Y^2\right]^{\frac{3}{2}}}$$

The point where the electric field is zero is found using a Root function.

X:=0.m This is the guess for the root.

x:=root($E_X$(X,0.m),X)

x=−0.00086.m This is the point on the x axis where the electric field is zero.

$E_X(x, 0.m) = 0 \cdot kg \cdot m \cdot sec^{-2} \cdot coul^{-1}$

This is the check that x is the solution of $E_x = 0$

The electrosurgical instrument is designed to provide consistent and accurate tissue treatment using a multipolar format on which at least two conductor pairs are used. The overall electrode body can be sized in accordance with the surgical modality required i.e.: Open, Minimal Access rigid and flexible endoscopic and/or micro translumen. In FIGS. 13a–b a tool is shown with an active electrode 100 and the return electrode is formed of multiple conductor components 102 selectively sized and geometrically designed for a dipolar RF energy source. The return electrode components are generally uniform in distribution and spacing from one another as is illustrated in the drawings so described. An extension of the design allows for further additional service ports for gas delivery (such as Argon) 104, suction/irrigation ports 106 and fibre light illumination sources 108 or other services to be provided to the surgical site and examples of tools including these features are included in FIGS. 13a–b. Each design can be formed into the required size for the surgical application being performed.

In use the active electrode couples energy to the tissue site via the resistive capacitive anode which is in effect the tissue and FIGS. 8a–b and 9a–b illustrate the field created between the tool working end 54 and the body tissue 96. A high frequency, potential difference is created both within the EM field 98 and the tissue when the active electrode 50 is contacted with a resistive capacitive element such as the tissue. A high-density electrical current is thus allowed to flow to the tissue until there is a potential impedance change, which is both resistive and capacitive in nature. The RF/EM field 98 uses a Radio frequency biphasic alternating waveform, which acts as a phased array and the excitation and radiation pattern is electronically controlled by the RF generator source, current density, beam intensity and directivity is controlled by the multipolar electrode arrangement.

This arrangement allows, in the dipolar arrangement, the ability for only the active electrode 50 to b in contact with the tissue for the current at the tool working end 54 to return via phased ion plasma which is formed between the electrodes of the tool and the tissue, effectively producing an 'Air Return" 99 between the tissue 96 and the return electrode 52 of the tool. Since the RF power required for phased ionisation is coupled to the active electrode 50, and thereby the tissue capacitively, through a RF generator, the flow of the net high-density current is significantly reduced thereby allowing the voltage drop between the electrodes and the tissue to increase. Optimisation of the plasma discharge is achieved by electrode geometry.

Ionised EM radiation is ejected within the time scale of a second phased RF cycle which depends upon the change in potential between the formation and ejection therefore for a given residence time of the ion field within the RF discharge and the energy is created by way of an ionised field.

Generally with this arrangement both positive ions and electrons are generated within the RF/EM Field. The difference in the mobility of these particles creates a self bias on the return electrode components which is then capacitively coupled to the active electrode. The degree of self-bias and directivity is controlled by the geometry of the active and return electrodes and particularly the relative surface area of the active electrode.

By adopting a dipolar configuration for the return electrodes 52 and in particular a degree of surface curvature at the end(s) the corona effect is both enhanced and shaped leading to current flow from the active electrode 50 to the tissue in a controlled manner without the need for the tissue to be physically contacted by both the active and return electrodes of the tool.

The dipolar configuration for the return electrode 52 also provides a distorted EM field around the exposed edges of the return electrode components and within the spacing between the active and return electrodes. This enhances the biphase field of ion/electron pairs since neutral biphased particles produce a dipole moment moving within the field which rapidly gains potential energy which, in turn, increases the EM/RF field. The return electrode components minimise axially charged particles, which leave in the direction of one or more of the return electrodes, since they gain variable energy within the main field, thus giving rise to a broad energy distribution.

FIG. 10 illustrates one embodiment of the use of the electrosurgical tool in accordance with the invention and an electrosurgical generator circuit which is for use with the electrosurgical tool disclosed in FIG. 6 with the generator shown to operate in a biphase generator circuit for use therewith.

A further potential usage for the tool in accordance with this invention is to use the same for Percutaneous transluminal Procedures and FIGS. 11a and b illustrate one such embodiment of the tool in which there is provided a connection 210 to an electrosurgical generator, a tool body 212 with operating buttons 214 and a lead in the form of a catheter 216 which at the working tip 218 has an active 220 and return 222 electrode arrangement. One particularly useful application of this embodiment is in relation to heart problems and to the lumen through which blood flows can narrow and if the lumen is sufficiently narrow the rate of blood flow is such that a thrombus or clot is formed. This extends rapidly into the surrounding blood through proteolytic action of thrombin and so atherosclerotic plaque in the lumen is a major predisposing factor. The tool in the embodiment herein described offers a solution whereby the flexible catheter allows the provision of electrosurgical energy for reducing occlusions located at a point in a vas (blood vessel) in tissue.

Thus when one considers that in one of the potential uses of the tool, laparoscopic electrosurgery, the view of the surgical field is constricted and the surgeon operates from the exterior of the patient's body usually using 14-inch (35-cm) remote instrumentation it will be appreciated that the tool in accordance with the current invention with its reduced risk of unintended burning and greater control is of advantage. The manipulation of tools of this type and tissue is based on magnified images of a 1.5-inch (4 cm) field, relayed from a miniature camera connected to the laparoscope and displayed on a video monitor. The very nature of the surgical environment—in which the active electrode is in close proximity to other conductive instruments and to tissue—can conventionally result in stray electrical current being transmitted to unseen tissue off the extended shaft of the remote laparoscopic instruments as has previously been discussed but this problem is significantly reduced by use of the tool in accordance with this invention.

What is claimed is:

1. An electrosurgical tool for operation in conjunction with a power supply and control means which controls the power supply to the tool, said tool having a first end from which depend electrical connections to the power supply, and the tool includes a supply or active electrode, and a return electrode, the ends of which electrodes positioned at the end of the tool opposing the first end of the tool, define the end of the tool for performing an electrosurgical function when positioned in proximity with the body tissue and characterised in that at that end of the tool, the working end of the active electrode is positioned to protrude beyond the end of the return electrode to contact with the body tissue and the return electrode is formed from a plurality of spaced electrode components; and wherein, the tool is used in conjunction with a control means for an electrosurgical generator which utilises dynamic impedance feedback and adaptive algorithm techniques together with a wave guided biphasic RF/EM energy to generate a phased energy field around the active electrode of the tool at the working end of the tool.

2. An electrosurgical tool according to claim 1 characterised in that the control means controls the power supply in relation to measured impedance of the body tissue during contact between the active electrode and body tissue.

3. An electrosurgical tool according to claim 1 characterised in that the active electrode is substantially surrounded along its length by the return electrode components.

4. An electrosurgical tool according to claim 3 characterised in that the return electrode formed by the components is substantially annular in cross section and the active electrode passes along the central passage defined by the same.

5. An electrosurgical tool according to claim 1 characterised in that the end of each of the return electrode components at the working end of the tool is curved and/or angled.

6. An electrosurgical tool according to claim 1 characterised in that the return electrode components are provided in pairs of phased negative and phased positive portions.

7. An electrosurgical tool according to claim 1 characterised in that the active electrode is axially spaced from the return electrode components.

8. An electrosurgical tool according to claim 7 characterised in that the spacing is maintained by providing an insulating material body between the active and return electrodes.

9. An electrosurgical tool according to claim 1 characterised in that the tool is provided with location means to allow the location and connection of the surgical working tip formation in contact with the active electrode.

10. An electrosurgical tool according to claim 1 characterised in that the tool is provided with location means to allow the location and connection of an active electrode with a working tip formation thereon.

11. An electrosurgical tool according to claim 1 characterised in that the working end of the tool is provided at the end of a catheter tube connected to the tool housing.

12. An electrosurgical tool according to claim 1 characterised in that the active electrode and return electrode are connected in parallel to the electrosurgical generator and the supply is split using a biphasic RF output and controlled in response to the impedance measurement of the active electrode and/or the body tissue.

13. An electrosurgical tool according to claim 1 characterised in that the biphasic array within the RF/EM field generated by the tool is used as the return pathway and the Radiofrequency [RF] energy is directed using impedance controlled by a biphasic RF/EM Field surrounding the active electrode.

* * * * *